United States Patent
Bruce et al.

(10) Patent No.: US 7,553,539 B2
(45) Date of Patent: *Jun. 30, 2009

(54) GRAIN FOR PROVIDING CELL GROWTH

(75) Inventors: Ingrid Bruce, Viken (SE); Lars Bruce, Viken (SE); Adam Bruce, Viken (SE)

(73) Assignee: Tigran Technologies AB, Malmo (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/415,431

(22) Filed: May 2, 2006

(65) Prior Publication Data

US 2007/0003752 A1    Jan. 4, 2007

Related U.S. Application Data

(63) Continuation-in-part of application No. 09/959,439, filed as application No. PCT/SE00/00802 on Apr. 28, 2000, now Pat. No. 7,056,577.

(30) Foreign Application Priority Data

Apr. 28, 1999    (SE)    .................................... 9901523

(51) Int. Cl.
   *B32B 3/26*    (2006.01)
   *A61F 2/28*    (2006.01)

(52) U.S. Cl. ............... 428/312.8; 428/315.5; 428/315.7; 428/305.5; 428/71; 428/76; 623/62.63; 623/23.52; 623/16.11

(58) Field of Classification Search .............. 428/312.8, 428/315.5, 315.7, 305.5, 71, 76; 623/23.52, 623/16.11, 23.63
See application file for complete search history.

(56) References Cited

U.S. PATENT DOCUMENTS

| 4,154,675 | A | 5/1979 | Jowett et al. |
| 4,318,990 | A | 3/1982 | Thomson et al. |
| 4,713,076 | A | 12/1987 | Draenert |
| 5,015,247 | A | 5/1991 | Michelson et al. |
| 5,015,256 | A | 5/1991 | Bruce et al. |
| 5,217,496 | A | 6/1993 | Bruce et al. |
| 5,282,861 | A | 2/1994 | Kaplan |
| 5,464,440 | A | 11/1995 | Johansson |
| 5,645,598 | A | 7/1997 | Brosnahan, III |
| 5,676,700 | A | 10/1997 | Black et al. |
| 5,986,169 | A | 11/1999 | Gjunter |
| 6,565,606 | B1 | 5/2003 | Bruce et al. |

(Continued)

FOREIGN PATENT DOCUMENTS

EP    0 159 036    10/1984

(Continued)

*Primary Examiner*—Hai Vo
(74) *Attorney, Agent, or Firm*—Smith, Gambrell & Russell, LLP

(57) ABSTRACT

The present invention relates to an irregularly shaped grain for providing ingrowth and growth of connective tissue as well as growth of other cell types leading to cluster of cells, tissues and parts of organs. Said grain includes multiple pores that are continuous through said grain, and openings of said multiple pores and ducts or passages interconnecting at least a portion of said multiple pores have a width of greater than about 10 μm. Said grain is preferably a metal or metal alloy. The invention also relates to different applications of the grains.

31 Claims, 5 Drawing Sheets

U.S. PATENT DOCUMENTS

Figure 1:
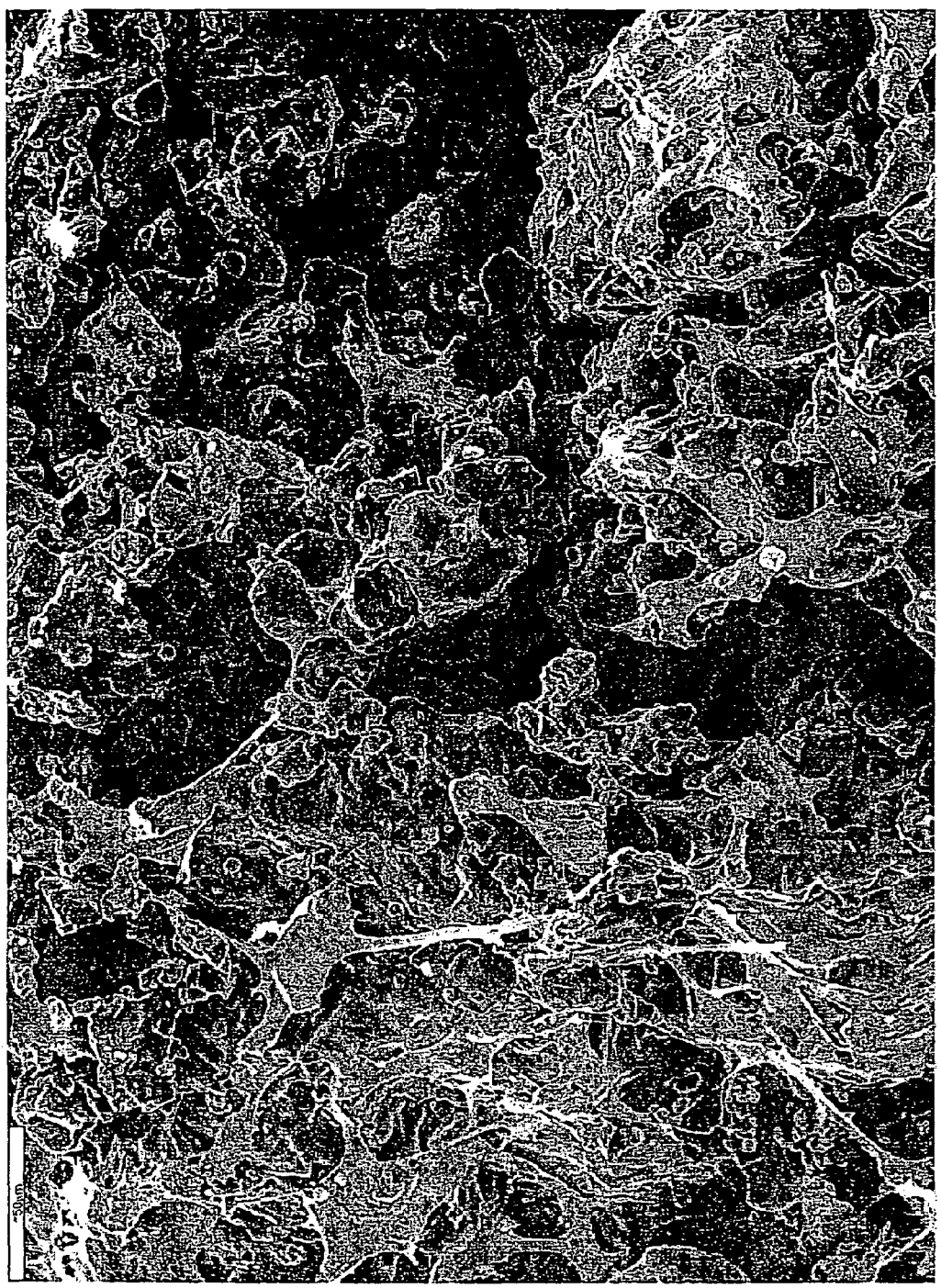

| | | |
|---|---|---|
| 6,599,620 B2 | 7/2003 | Fujita et al. |
| 7,056,577 B1 | 6/2006 | Bruce et al. |
| 2003/0220696 A1 * | 11/2003 | Levine et al. ............ 623/17.17 |

FOREIGN PATENT DOCUMENTS

| | | |
|---|---|---|
| EP | 0 267 624 | 5/1998 |
| EP | 0 856 299 | 8/1998 |
| SE | 0 462638 | 8/1990 |
| SE | 98/515572 | 9/1998 |
| SE | 98/03078-6 | 3/2000 |
| WO | WO 93/13815 | 7/1993 |
| WO | WO 97/24084 | 10/1997 |
| WO | WO 98/16 267 | 4/1998 |
| WO | WO 98/30620 A1 | 7/1998 |
| WO | WO 99/13478 | 3/1999 |
| WO | WO 99/34845 | 7/1999 |
| WO | WO 00/13615 | 3/2000 |
| WO | WO 00/64505 | 11/2000 |
| WO | WO 2005/030283 | 4/2005 |

* cited by examiner

GRAIN FOR PROVIDING CELL GROWTH

This application is a Continuation In Part on U.S. patent application Ser. No. 09/959,439 filed Dec. 3, 2001, which represents a national stage filing of PCT/SE00/00802 having an international filing date of 28 Apr. 2000 (published in English as WO 00/64504) and which claimed Paris Convention priority to SE 9901523-2, with each being herein incorporated by reference.

FIELD OF THE INVENTION

The present invention relates an irregularly shaped grain for providing ingrowth and growth of connective tissue as well as growth of other cells as disclosed herein.

BACKGROUND ART

SE-B-462,638 discloses a means for fixing an elongate prosthesis, such as the stem of a femural prosthesis, to living tissue which defines a cavity in which a length of the prosthesis is received with a gap to the boundary of the cavity. Essentially the entire gap is filled with loose, but packed grains of a biocompatible material, said grains interlocking. As an example of granular material titanium is mentioned, and the grains are stated to be irregular, essentially non-elastic and preferably porous, the latter property being said to bind growth of bone tissue which has grown from the osseous wall. The porosity has been obtained by blowing gas through a melt of the granular material.

U.S. Pat. No. 5,217,496 discloses an implant suited for use in living bone tissue and comprising a support of titanium having a porous outer surface and an attached layer of a mixture consisting of disintegrated living bone tissue and titanium powder. The mixture is supplied with nutriment which makes the disintegrated bone tissue grow and form tissue which connects the disintegrated bone tissue and the titanium powder with each other and with the support.

U.S. Pat. No. 5,676,700 discloses biocompatible structure elements for repair, reinforcement and replacement of bone tissue, said elements being indicated to form an osteoconductive or osteoinductive matrix in a bone tissue cavity. The material of the elements can be titanium and the elements are said advantageously to be microporous for ingrowth of natural bone.

In the above documents, porosity of biocompatible materials is thus pointed out to cause something favorable for binding of bone tissue.

SUMMARY OF THE INVENTION

According to the present invention, it has surprisingly been found that a predetermined measure of the porosity of biocompatible material is in fact a decisive factor as regards the growth rate of connective tissue. It has been found that while surface porosity certainly allows binding of connective tissue, a significantly increased growth rate of connective tissue and a larger amount of connective tissue are obtained and, thus, a significantly improved anchoring and strength of connective tissue on the biocompatible material if the body, such as a grain, of the biocompatible material is continuously porous, the porosity of the body has a minimum limit value.

The above said also applies to the growth of cells other than connective tissue cells. Thus, it has also been found according to the present invention that other cells such as stem cells, osteocytes, astrocytes, human renal epithelial cells, coronary artery smooth muscle cells (CASMC), chondrocytes, chondrosarkoms, hepatocytes, breast cells, spinal nerve cells, nerve cells, liver cells, bladder cells, dermal cells, ear cells, heart cells, kidney cells, pancreas cells, and urethra cells can be grown very well on a body such as a grain of a biocompatible material if the material is continuously porous and the porosity of the body has a minimum limit value.

The present invention, in one aspect, relates to an irregularly shaped grain for providing ingrowth and growth of connective tissue, and said grain being made of a plastic or essentially non-elastic biocompatible implant material, wherein said grain includes multiple pores that are continuous through said grain, and openings of said multiple pores and ducts or passages interconnecting at least a portion of said multiple pores have a width of greater than about 10 µm, and wherein said grain is a metal or metal alloy.

The present invention, in another aspect, relates to an irregularly shaped grain for providing ingrowth and growth of connective tissue, said grain being made of a plastic or essentially nonelastic biocompatible material, wherein said grain includes multiple pores that are continuous through said grain, and openings of said multiple pores and ducts or passages interconnecting at least a portion of said multiple pores have a width of greater than about 10 µm, and wherein said multiple pores are filled with a decomposable material, and wherein said grain is a metal or metal alloy.

The present invention, in a further aspect, relates to an irregularly shaped grain for providing ingrowth and growth of connective tissue, said grain being made of a plastic or essentially nonelastic biocompatible material, wherein said grain includes multiple pores that are continuous through said grain, and openings of said multiple pores and ducts or passages interconnecting at least a portion of said multiple pores have a width of greater than about 10 µm, wherein said grain has a coral structure, and wherein said grain is a metal or metal alloy.

The present invention, in a further aspect, relates to an implant comprising a plurality of grains and a casing, said grains providing ingrowth and growth of connective tissue, said grains being made of a plastic or essentially non-elastic biocompatible material, wherein said grains include multiple pores that are continuous through the grain, and openings of said multiple pores and ducts or passages interconnecting at least a portion of said multiple pores have a width of greater than about 10 µm, and wherein said grain is a metal or metal alloy.

The present invention, in a further aspect, relates to an irregularly shaped grain for providing cell growth including ingrowth and/or growth of cells in and on said grain, and said grain being made of a plastic or essentially non-elastic biocompatible implant material, wherein said grain includes multiple pores that are continuous through said grain, and openings of said multiple pores and ducts or passages interconnecting at least a portion of said multiple pores have an average width of greater than about 10 µm, and wherein said grain is a metal or metal alloy.

In one embodiment of the invention said cells and grains are encapsulated in a microcapsule. Such microcapsule may for example be made of alginate. By encapsulating the cells and the grains in a capsule growth of the cells is provided in the capsule. This could beneficial in case if implantation.

The present invention, in another aspect, relates to an irregularly shaped grain for providing cell growth including ingrowth and/or growth of cells in/on said grain, said grain being made of a plastic or essentially nonelastic biocompatible material, wherein said grain includes multiple pores that are continuous through said grain, and openings of said multiple pores and ducts or passages interconnecting at least a portion of said multiple pores have an average width of greater than about 10 μm, and wherein said multiple pores are filled with a decomposable material, and wherein said grain is a metal or metal alloy.

The present invention, in a yet further aspect, relates to an irregularly shaped grain for providing cell growth including ingrowth and/or growth of cells in/on said grain, said grain being made of a plastic or essentially nonelastic biocompatible material, wherein said grain includes multiple pores that are continuous through said grain, and openings of said multiple pores and ducts or passages interconnecting at least a portion of said multiple pores have an average width of greater than about 10 μm, wherein said grain has a coral structure, and wherein said grain is a metal or metal alloy.

The present invention, in a yet further aspect, relates to an implant comprising a plurality of grains and a casing, said grains providing cell growth including ingrowth and/or growth of cells in/on said grain, said grains being made of a plastic or essentially non-elastic biocompatible material, wherein said grains include multiple pores that are continuous through the grain, and openings of said multiple pores and ducts or passages interconnecting at least a portion of said multiple pores have an average width of greater than about 10 μm, and wherein said grain is a metal or metal alloy.

The present invention, in a yet further aspect, relates to a method of growing cells in vitro, said method comprising the steps of:

providing a cell suspension of cells;

bringing the cell suspension and at least one grain into contact, said at least one grain is made of a plastic or essentially non-elastic biocompatible material, and includes multiple pores that are continuous through the at least one grain, and openings of said multiple pores and ducts or passages interconnecting at least a portion of said multiple pores have an average width of greater than about 10 μm, and wherein said at least one grain is a metal or metal alloy; and allowing the cells to grow in/or said at least one grain in a growth promoting environment.

An advantage of the invention is that the provided cell growth may be of cells of different origin. For example a patient in need of a certain kind of cell tissue, part of a tissue, organ or cell producing substance in the body can have its own cells removed from the body and grown outside the body. When the desired production or growth has been obtained, the cell cluster or tissue can be implanted into the patients body again. In this way typical rejection is avoided. In accordance with the invention such rejection can be avoided since the patients own cells are used as the growth cell material. A patient in need of implantation of an organ or an entity thereof today has problems with rejection of the implanted organ and must take immunosuppressive drugs in order to avoid rejection. Such medication can be lifelong and is a great burden on the patient. Such rejection and such strong medication can at least be reduced in accordance with the invention.

The present invention, in another aspect, relates to a method of treatment of a protein or hormone deficiency in an animal subject, said method comprising the steps of:

providing a cell suspension of cells capable of producing a protein or a hormone, and at least one grain, said at least one grain is made of a plastic or essentially non-elastic biocompatible material, and includes multiple pores that are continuous through the at least one grain, and openings of said multiple pores and ducts or passages interconnecting at least a portion of said multiple pores have an average width of greater than about 10 μm, wherein said at least one grain is a metal or metal alloy; and implanting said cell suspension and said at least one grain into the animal subject, whereby the cells grow in/or said at least one grain in the animal subject and produce the hormone or protein in order to compensate for the hormone or protein deficiency.

In the present context the phrase "animal subject" is intended to mean both an human and an animal.

Thus, the cells used in the above mentioned method of treatment of a protein or hormone deficiency have a therapeutic function. Non-limiting examples of said protein or hormone is erythropoeitin, growth hormone (GH), immunosuppressive substances and immunostimulating substances. Any other hormone or protein suitable for growth in a grain in accordance with the invention may naturally be performed and in the scope of the invention.

The present invention can also be used for growing therapeutic cells. Therapeutic cells are, in the present invention, defined as any cell or cell type having the capability of producing a therapeutic product of interest. Examples of such therapeutic cells are stem cells, recombinant cells and cells genetically modified. For example, a gene sequence encoding a desired therapeutic polypeptide or protein product (or a therapeutic nucleic acid product) can have been introduced, e.g. in the form of an expression cassette, into a given cell. This cell can then be cultured and grown on the biocompatible material of the present invention for expression and production of the encoded therapeutic product. Thus, any cell having the capability of producing a therapeutic product when cultured under suitable conditions can be grown on the biocompatible material of the invention to increase the growth rate of the cells and thereby increase the expression of the desired therapeutic product. The cells to e.g. be genetically engineered can be stem cells or cells selected from the previously mentioned cells. In any case, all these therapeutic cells can be grown very well on a body of a grain of a biocompatible material if the material is continuously porous and the porosity of the body has a minimum limit value.

Non-limiting examples of therapeutic products that can be produced and secreted by therapeutic cells grown on a biocompatible material of the invention includes recombinant proteins, preferably recombinant mammalian proteins and more preferably recombinant human proteins. Such protein can be selected from insulin, erythropoietin, glucagon-like peptide 1 or 2, interleukins such as interleukin 2, interleukin 15, hormones, cytokines, growth factors, immunostimulating proteins, immunosuppressing proteins, proteins involved in the complement and coagulation cascades, such as tissue factor, factor VII and VIIa, inactivated factor VIIa, factor X, growth hormone (GH), insulin-like growth factor 1 (IGF-1), growth Hormone Release Hormone (GHRH), vascular endothelial growth factor (VGEF), fibroblast growth factor (FGF), endostatin, angiostatin, granulocyte-macrophage colony-stimulating factor, elastase inhibitor, human serum albumin, glucagon, hepatitis B surface antigen, kalikrein inhibitor, hirudin, platelet-derived growth factor, epidermal growth factor analog and urate oxidase.

Thus, a human or animal suffering from a protein or hormone deficiency may be treated with a cell suspension comprising the required cells and the grains as disclosed herein. When the cell suspension has been implanted in the body the cells produce the desired protein or hormone. Thus, the protein or hormone deficiency will be treated in place in the body. The cell suspension and at least one grains may be encapsulated in a microcapsule, whereby the required protein or hormone being produced inside the capsule, and as time goes the capsule preferably will be dissolved and the protein and hormone released, i.e. sustained release.

This aspect of the present invention can also be applied for transplanting cells producing other desired (therapeutic) products besides proteins and hormones.

The present invention, in a yet further aspect, relates to a method of killing and/or inhibiting the growth of cancer cells in an animal body, said method comprising the steps of:

providing a cell suspension of cells capable of producing a substance inhibiting the growth of cancer cells and/or killing cancer cells and at least one grain, said at least one grain is made of a plastic or essentially non-elastic biocompatible material, and includes multiple pores that are continuous through the grain, and openings of said multiple pores and ducts or passages interconnecting at least a portion of said multiple pores have an average width of greater than about 10 μm, wherein said at least one grain is a metal or metal alloy; and delivering said cell suspension and said at least one grain in connection to a cancer site in said animal subject, whereby the cells growth in/or said at least one grain in the animal subject and produce said substance inhibiting the growth of and/or killing said cancer cells.

The bacteria used in the combination above of the method acts on the cancer cells by inhibiting their further growth and by killing the cells. This may be done by the bacteria themselves as well as by a toxin produced by the cells. An effect is achieved on both the further growth of the cells as well as on the existing cells.

In this aspect of the present invention, the bacteria cells may be replaced with any other cell types capable, when grown on the at least one grain in the animal body of producing a substance that inhibits the growth of the cancer cells and/or kills the cancer cells. For example, cells producing toxins, immunostimulating molecules, a growth inhibiting products can be used according to the invention.

Thus, the present invention relates to the growth of different cells, such as connective tissue cells, on bodies such as grains having a width of greater than about 10 μm. The growth of these cells, with ingrowth and growth of the different cell types on the bodies, is possible on bodies as disclosed in U.S. patent application Ser. No. 09/959,439. The growth of the different cell types is also improved with increased growth rate of the cells on the biocompatible material if the body, such as a grain, of the biocompatible material is continuously porous, the porosity of the body has a minimum limit value.

By letting cells grow on bodies such as grains having a width of greater than about 10 μm as disclosed in patent application Ser. No. 09/959,439, it is possible to obtain in/or on the bodies a grown cluster of cells, part of a tissue, an entire tissue, part of an organ or an entire organ. These cluster of cells, part of a tissue, an entire tissue, part of an organ or an entire organ grown on the bodies such as grains having a width of greater than about 10 μm may then be transplanted to an animal, preferably a mammalian animal, such as dog, cat, horse, cow, sheep, ape, monkey, and more preferably a human in need of such transplantation of cells, cluster of cells, tissue, part of tissue, part of organ and organ.

By "continuously porous" is here meant a porosity which allows connective tissue or other cells presented herein to grow through the porous body, such as the grain of biocompatible material. According to the invention, such porosity results in cavities in the body which are interconnected by ducts, passages, so that growth of connective tissue onto a part of the outer surface of the body allows the growth to continue through the body and out through other parts of the outer surface of the body. By cavity is meant indentations, pits, pockets of an arbitrary shape, and the ducts, passages, interconnecting these cavities can have an arbitrary form and constitute part of the cavities. Examples of such a structure can be found in nature in corals or drips tone caves.

By "continuously porous" is also meant herein that the above also applies to the other types of cells mentioned herein. It is also possible that a chain of connected cells is formed in the cavities of the grain.

By "providing cell growth including ingrowth and growth of cells in/on said grain" is herein meant that the cells are able to grow, i.e. propagate, and survive on and in the grain in the particular growth medium. The propagation can continue until the desired amount of cluster of cells or part of tissue has formed.

By minimum limit value is here meant an opening of an indentation, pit, pocket and a duct opening having a width of > about 10 μm. A smaller opening dimension restricts or inhibits the growth of cells, probably because the supply of nutriment is inhibited. In fact there is no upper limit of the porosity of the body. The upper limit is rather determined by the strength properties of the body. However, in an embodiment of the parent invention the openings of said multiple pores and ducts or passages interconnecting at least a portion of said multiple pores have a width of greater than about 10 μm and equal to or less than 50 μm. In one embodiment of the present invention the openings of said multiple pores and ducts or passages interconnecting at least a portion of said multiple pores have a width of greater than about 10 μm and equal to or less than about 200 μm, since about 200 μm is the maximum value for a cluster or an aggregate of cells growing in/on a grain according to the invention.

According to the invention, cavities can be allowed to form of surface pores in bodies which are located next to each other and have open surface pores, so that the surface pores in one body form a cavity or duct/passage with the surface pores in the other body.

According to the invention, it has also been found that a brittle biocompatible material, such as hydroxylapatite, is not optimal for the purposes of the invention since such a material easily decomposes. Decomposed parts of a body of biocompatible material cause an unfavorable inflammatory reaction which inhibits the growth of cells.

According to the invention, a metallic material or non-brittle composites are therefore chosen, where natural material, such as hydroxylapatite, bioceramics etc., can be included as a component in the material of the porous body and another component, such as plastic, guarantees plasticity. The body material according to the invention should in fact be plastic or non-essentially elastic.

Titanium (titanium dioxide) is advantageously selected as metallic material. The porosity of the titanium body is advantageously achieved by blowing gas through a melt of titanium. This makes it possible to produce titanium grains, as mentioned in SE-B-462,638. There are as well other methods for producing titanium grains, e.g. by the well known Hunter process or Kroll process.

The requirement as to porosity as stated above is, however, not automatically satisfied by blowing gas through a melt of metal. According to the invention, a check is therefore made of the porosity of the body/grain/grains obtained in this manner to ensure that it/they satisfies/satisfy the requirement. The check can be carried out, for example, by means of fluoroscopy at a suitable wavelength and a TV receiver and automatic separation (e.g. from a conveyor belt) of grains that do not satisfy the above mentioned requirement. Electron microscopy is another method which is possible to use in this sense.

The above limit value of > about 10 μm in one embodiment of the invention relates to connective tissue. The above limit value of > about 10 μm in a further embodiment of the invention relates to the ingrowth and growth of the other cell types mentioned herein.

A porous body, such as a grain, according to the invention can be implanted in a living body, such as a mammalian body, including a human body, for filling a cavity, as replacement, after growth of relevant tissue or cluster of cells in vivo. A porous body according to the invention can also serve as a base for preculturing of connective tissue or any other cells as disclosed herein in vitro and/or be filled with a nutrient solution containing, inter alia, growth factors in vitro for subsequent implanting in living tissue.

The porous body can be filled with a decomposable material, for example of a so-called matrix of the natural material. Examples of such natural matrices are gels of collagen, fibrin, starch, hydroxylapatite and other ceramics and hyaluronic acid. According to the invention, this matrix is decomposed to be replaced with the ingrowing cells mentioned herein. The ingrowth of cells can be further stimulated if growth-stimulating substances are added to the decomposable material, above all growth factors such as TGF beta (Transforming Growth Factor beta). The pores in the body according to the invention can be moved with the gel material, e.g. by suction, before the material is ready-gelled.

Smaller bodies, grains according to the invention can be enclosed in a casing, flexible or rigid, for producing an implant. For example, grains according to the invention can be enclosed in a rigid sleeve so as to form, together with the sleeve, a spinal implant, see e.g. the sleeve in U.S. Pat. No. 5,015,247. The sleeve can be formed like a tube or what is referred to as a hollow fiber for the growth of spinal nerve cells or nerve cells. In such an implant, ruptured nerve endings are possible to link to each other and grow together. Other possibilities of enclosing in a casing are disclosed in SE 9803078-6. The casing has openings to allow ingrowth and growth of biological cell material to and from the grains, through the casing. Grains according to the invention can be mixed with decomposed biological tissue.

A further embodiment of the invention is the combination of a grain according to the invention and a bioartificial implant according to WO05/030283, whereby the grains are encapsulated in the implant.

Figure 2:
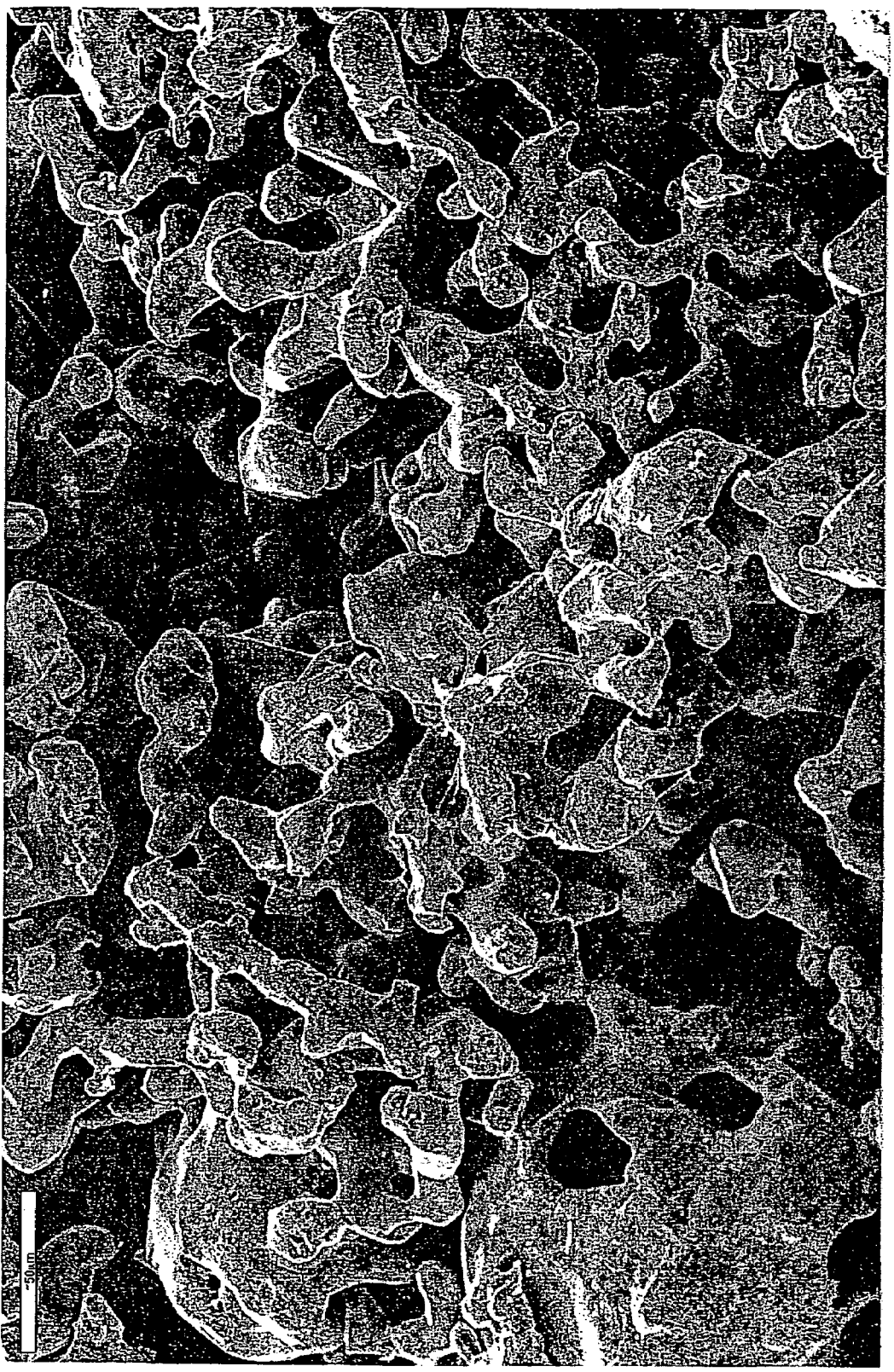

Embodiments of the invention are illustrated in the accompanying Figures which are electron microscope images and of which FIG. 1 shows a porous structure according to the invention and FIG. 2 shows another porous structure according to the invention of the outer surface of a titanium grain.

Figure 3:

FIG. 3 is an image of a thin section of a titanium grain with porosity according to the invention. All images are made of an irregular grain or granule which has been removed from the femur in a human body after implanting using a vibration technique which is described in more detail in SE-B-462,638.

Figure 4:
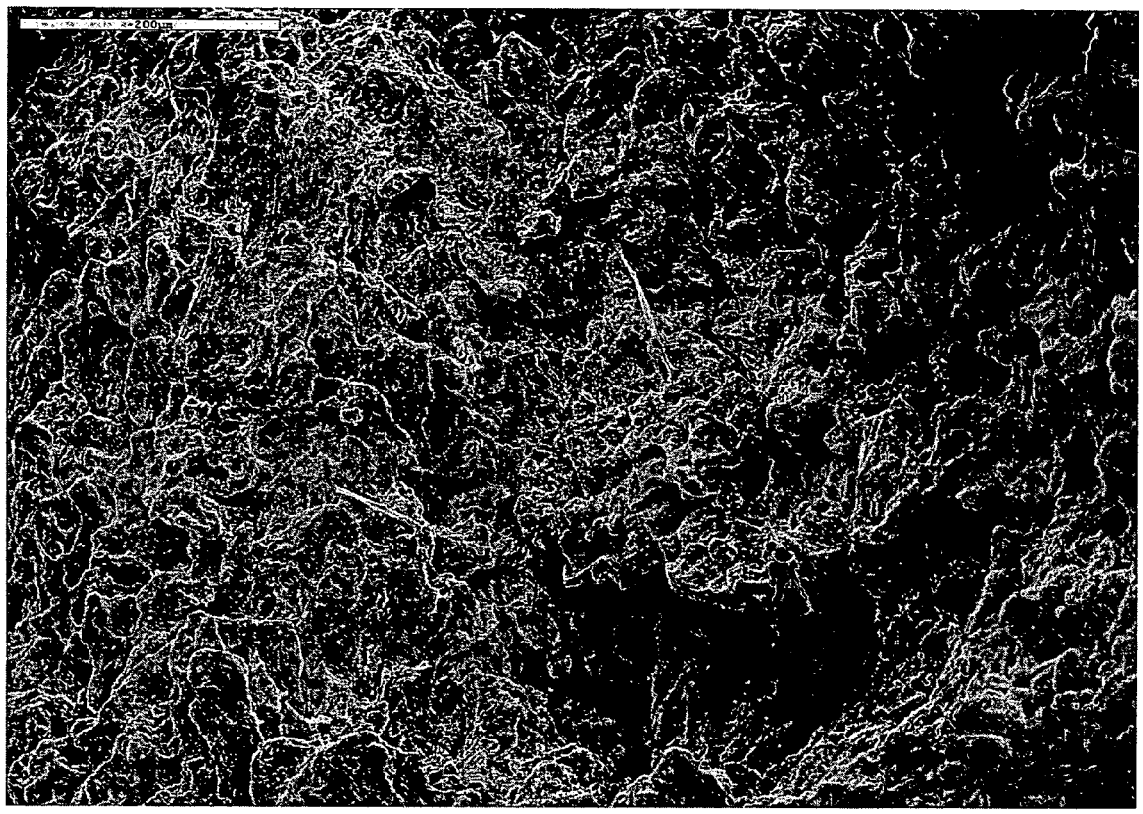

FIG. 4 illustrates astrocytes which have intersected and penetrated a grain according to the invention. The grain structures have been provided by blowing gas through a melt of titanium and applying the above-mentioned quality check. The image shows the astrocytes after a 6 weeks growth. Fine cells can be seen over large areas.

Figure 5:
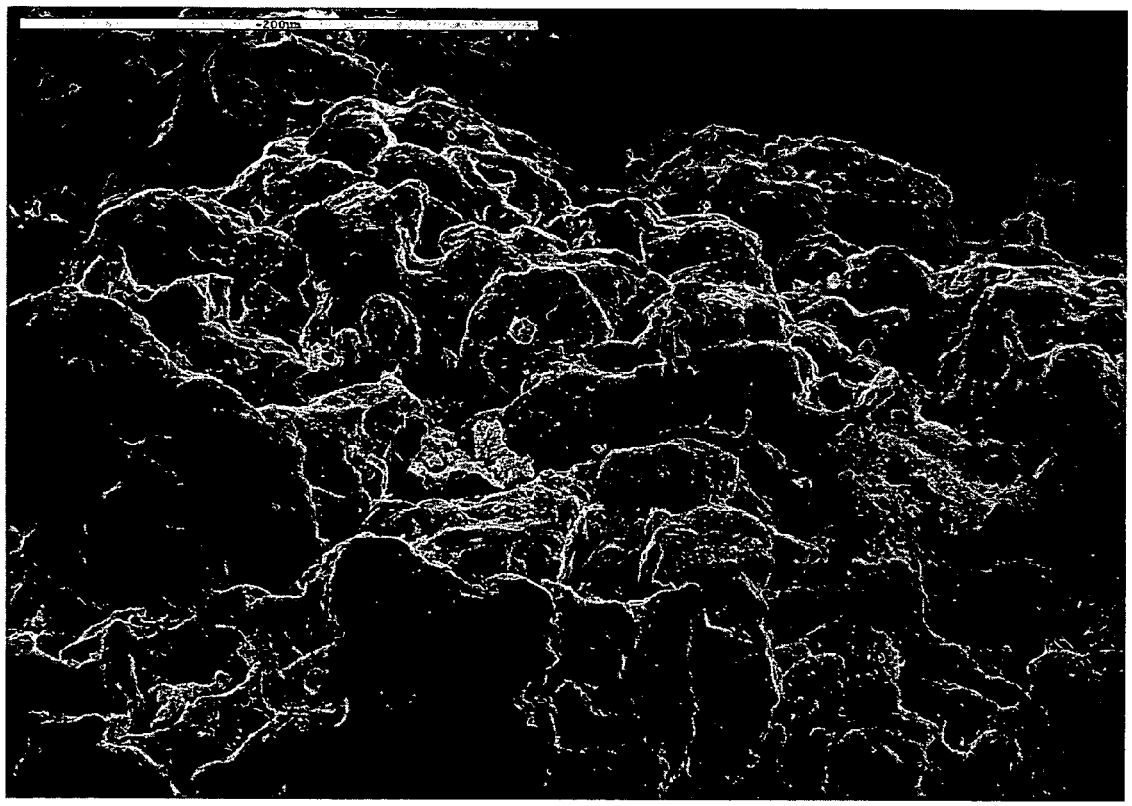

FIG. 5 illustrates kidney epithet cells which have intersected, penetrated a grain according to the invention. A lot of cells can be seen. The grain has been prepared as stated under FIG. 4.

CULTURING OF DIFFERENT CELL TYPES

According to the present invention, a variety of cells can be grown and/or cultured on the bodies according to U.S. patent application Ser. No. 09/959,439. The following experiments for growing different cells on the grains having a width of greater than about 10 μm have been performed for the growth of osteocytes, astrocytes, human renal epithelial cells, coronary artery smooth muscle cells (CASMC), osteosarkom and chondrosarkom, of which the last one showing the possibility to grow chondrocytes as well. However, other types of cells such as those mentioned above could also be grown, like for instance hepatocytes. Further, cells of spinal nerve, nerve, breast, liver, bladder, skin, ear, heart, kidney, pancreas and urethra or connective tissue, as well as stem cells, can also be grown on grains having a width of greater than about 10 μm. Furthermore, the growth experiments have been performed in vitro, but the present invention can be used for culturing and growing the cells in vivo as well.

Further, these cells, cluster of cells, part of a tissue, an entire tissue, part of an organ or an entire organ grown on the bodies such as grains having a width of greater than about 10 μm may then be transplanted into an animal, preferably a mammalian animal, such as dog, pig, horse, cat, ape, monkey, and more preferably a human in need of such transplantation of cells, cluster of cells, tissue, part of tissue, part of organ and organ.

The present invention can also advantageously be used for growing therapeutic cells. Therapeutic cells are, in the present invention, defined as any cell or cell type having the capability of producing a therapeutic product of interest. Examples of such therapeutic cells are stem cells, recombinant cells and cells genetically modified. For example, a gene sequence encoding a desired therapeutic polypeptide or protein product (or a therapeutic nucleic acid product) can have been introduced, e.g. in the form of an expression cassette, into a given cell. This cell can then be cultured and grown on the biocompatible material of the present invention for expression and production of the encoded therapeutic product. Thus, any cell having the capability of producing a therapeutic product when cultured under suitable conditions, in vitro or in vivo, can be grown on the biocompatible material of the invention to increase the growth rate of the cells and thereby increase the expression of the desired therapeutic product. The cells to e.g. be genetically engineered can be stem cells or cells selected from the previously mentioned cells. In any case, all these therapeutic cells can be grown very well on a body of a grain of a biocompatible material if the material is continuously porous and the porosity of the body has a minimum limit value.

Non-limiting examples of therapeutic products that can be produced and secreted by therapeutic cells grown on a biocompatible material of the invention includes recombinant proteins, preferably recombinant mammalian proteins and more preferably recombinant human proteins. Such protein can be selected from insulin, erythropoietin, glucagon-like peptide 1 or 2, interleukins, hormones, cytokines, growth factors, immunostimulating proteins, immunosuppressing proteins, proteins involved in the complement and coagulation cascades, such as tissue factor, factor VII and VIIa, inactivated factor VIIa, factor X.

The following culturing experiments will describe the present invention in more detail, but are not to be interpreted as a limitation of the invention.

EXPERIMENTS

Different cells were grown on the grains to evaluate how well they grew, i.e. propagation, on and into the indentations, pits or pockets of the bodies. The bodies or grains were bodies according to U.S. patent application Ser. No. 09/959,439, and in this particular case the grains are made of titanium or titanium alloy.

The different cells tested for growth were:
1) osteocytes
2) osteosarkom
3) chondrosarkom
4) astrocytes (see FIG. 1)
5) human renal epithelial cells (see FIG. 2)
6) coronary artery smooth muscle cells (CASMC)

The different cells originated from different sources and they were all commercially available. The osteocytes were produced by the applicant according to a standard technique, but the other cells were purchased from ATCC and Clonetics and had the following product numbers:
2) osteosarkom (ATCC CRL-2098)
3) chondrosarkom (ATCC HTB-94)
4) astrocytes (Clonetics CC-2565)
5) human renal epithelial cells (Clonetics CC-2554)
6) coronary artery smooth muscle cells (CASMC) (Clonetics CC-2583)

The different cell culturing media used were according to the following:
1) osteocytes:
450 ml MEM alpha medium (Gibco 22561-021)
10% FCS (Integro b.v. via Saveen)
10% NHS (Blodcentralen MAS 3392)
10 nM dexametasone (ICN 194561)
25 mg L-ascorbine (Sigma A-7506)
1.05 g β-glycerophosphate (ICN 102893)
1% penicillin-streptomycin solution (Sigma P-0781)
2) ostesarkom:
450 ml RPMI 1640 (Gibco 21875-034)
10% FCS (Integro b.v. via Saveen)
1% penicillin-streptomycin solution (Sigma P-0781)
3) chondrosarkom:
450 ml Leibovitz L-15 (Gibco 11415-049)
10% FCS (Integro b.v. via Saveen)
1% penicillin-streptomycin solution (Sigma P-0781)
4) astrocytes:
Purchased medium with additives (Clonetics CC-3186)
5) human renal epithelial cells:
Purchased medium with additives (Clonetics CC-3111)
6) coronary artery smooth muscle cells (CASMC):
450 ml DMEM (Sigma D-7777)
10% FCS (Integro b.v. via Saveen)
10% NHS (Blodcentralen MAS 3392)
1% penicillin-streptomycin solution (Sigma P-0781)

Before growing or culturing the cells on the bodies or grains can be performed, these grains can be pretreated. This pretreatment of the grains was performed by:
As many grains as required for the specific experiment was put into a 50 ml beaker. Absolute alcohol (99.5%, Kemetyl) was poured into the beaker and the beaker was allowed to stand for an hour.
The alcohol was aspirated with a water suction apparatus.
The grains were shaken out onto a napkin. The grains are allowed to lie on the napkin until the alcohol evaporated. Gloves were used for safety.
When the grains were dry, they were moved to a autoclavable storage vessel. Autoclavation was performed.

All the experiments with the cells were performed in a sterile bench (LaminAir HB 2448). The pretreatment of the grains described above was performed in a laboratory and all the experiments below were performed in a sterile bench.

The cell culturing experiments on the grains were performed according to the below:

Material
Culturing plates 24 wells (Sarstedt 83 1836)
10 ml sterile pipettes (Sarstedt 86.1254.001)
The correct culturing medium in respect to the different cell types according to above.
Grains pretreated according to above.
Sterile spoon.
Bürker chamber.
Cryotube (Sarstedt 72.694.006).
NaCaca buffer: 0.2M Sodium cacodylate (Sigma C0250) pH set at 7.15 with HCl (BDH 45002)
Fixation buffer: 2.5% glutaraldehyde (Sigma G7651) in NaCaca buffer
50% ethanol
70% ethanol
95% ethanol (Kemetyl)
99.5% ethanol (Kemetyl)
Culturing flasks T-25 (Sarstedt 83.1810)
T-75 (Sarstedt 83.1813)
T-175 (Sarstedt 83.1812)
Sterile PBS (Gibco 14190-094)
Trypsin-EDTA (Gibco 25300-054)
FCS (Integro .b.v. via Saveen)
Water suction apparatus Procedure
PBS, FCS and the medium was heated in water bath to 37° C.
The medium was thoroughly aspirated with the water suction apparatus. Then washing was performed twice with PBS. Finely a thoroughly aspiration was performed.
Trypsin-EDTA was added: 2 ml to T-25
3.5 ml to T-75
5 ml to T-175
Incubation was performed at 37° C. for 3 minutes.
The flask was removed from the incubator and the bottom was pounded. Whether the cells had loosen from the bottom or not was investigated in a microscope. The same amounts of FCS and trypsin-EDTA were added. Then it was removed to 15 ml tubes and centrifugation was performed at 1000 rpm for 5 minutes.
The cells were made to a slurry in the medium. Then they were counted in a Bürker chamber. Dilution was then performed until the decided value of number of cells/ml according to the experiment protocol was obtained.
Pipetation of 1 ml cell suspension/well in the cell culturing plate was performed. Some grains were put in per well.
The plate was allowed to stand in the incubator at 37° C., 5% $CO_2$.

After the number of weeks according to the experiment protocol, the grains were taken out and put in cryotubes. 1 ml fixation buffer was held thereon and fixation was performed over night.

The fixation buffer was aspirated and washing was performed twice with NaCaca buffer. The grains were kept in the NaCaca buffer until dehydration.

Dehydration: 50% ethanol 2×10 minutes
70% ethanol 2×10 minutes
95% ethanol 2×10 minutes
99.5% ethanol 2×20 minutes The grains were then kept in 99.5% ethanol in a fridge.

All cells were cultured at 37° C. in a humidified atmosphere containing 5% $CO_2$. The medium in all cells is refreshed every 2-3 days. The grains were taken out after 2, 3, 4, 6, 8, and 12 weeks, respectively. The evaluations were registered in the experiment protocol.

Evaluation

The grains were evaluated in an electron microscope with the SVEP method.

Results

It can be seen from an examination of the above experiments that already after 2 weeks that some of the cells have already started to grow and formed a fine structure on the grains according to the invention. This can be established in view of the fact that the cells are still alive and started forming structures. After 6 weeks the majority of the cells have grown even further. In FIG. 1 it can be observed how the astrocytes have grown after 6 weeks. Fine cells can be seen over large areas. Further, FIG. 2 illustrates kidney epithet cells which have intersected, penetrated a grain according to the invention after 8 weeks of growth. A lot of cells can be seen. A fine structure of the growing cells over the surface can be seen.

In view of the large organ deficiencies world wide it is contemplated that the grains according to the invention may be used for both in vitro and in vivo growth of cells into tissues, part of tissues or organs.

The invention claimed is:

1. An irregularly shaped grain for providing ingrowth and growth of connective tissue, and said grain being made of a plastic or essentially non-elastic biocompatible implant material, wherein said grain includes multiple pores that are continuous through said grain, and openings of said multiple pores and ducts or passages interconnecting at least a portion of said multiple pores have a width of greater than about 10 µm, and wherein said grain is a metal or metal alloy.

2. The grain as claimed in claim 1, wherein said grain is made of titanium or titanium alloy.

3. An irregularly shaped grain as claimed in claim 1, wherein said multiple pores are filled with a decomposable material.

4. The grain as claimed in claim 3, wherein the decomposable material contains growth-stimulating substances.

5. The grain as claimed in claim 3, wherein said decomposable material includes a matrix of natural material.

6. The grain as claimed in claim 5, wherein said matrix of natural material includes a gel of at least one of collagen, fibrin, starch, hydroxylapatite or similar ceramics and hyaluronic acid.

7. An irregularly shaped grain as claimed in claim 1, wherein said grain has a coral structure.

8. The grain as claimed in claim 1, wherein said grain size is less than 10 mm.

9. An aggregate of grains, which includes grains as claimed in claim 1.

10. An aggregate of grains for providing ingrowth and growth of connective tissue, which aggregate consists essentially of grains according to the grain of claim 1.

11. The aggregate as claimed in claim 10, wherein said aggregate of grains is configured for implant use.

12. The grain as claimed in claim 1, wherein said multiple pores of said grain are randomly distributed.

13. The grain as claimed in claim 1, wherein the multiple pores that are continuous are sized to connective tissue to grow through said grain.

14. The grain as claimed in claim 1, wherein said grain is of a monolithic structure with said multiple pores extending into the surface of that monolithic structure.

15. An implant comprising a plurality of grains and a casing, said grains providing ingrowth and growth of connective tissue, said grains being made of a plastic or essentially non-elastic biocompatible material, wherein said grains include multiple pores that are continuous through the grain, and openings of said multiple pores and ducts or passages interconnecting at least a portion of said multiple pores have a width of greater than about 10 µm, and wherein said grain is a metal or metal alloy.

16. The implant as claimed in claim 15, wherein the casing is a rigid cylindrical sleeve or a hollow fibre for producing a spinal implant.

17. An irregularly shaped grain made of a plastic or essentially non-elastic biocompatible implant material, wherein said grain includes multiple pores that are continuous through said grain, and openings of said multiple pores and ducts or passages interconnecting at least a portion of said multiple pores have an average width of greater than about 10 µm, and wherein said grain is a metal or metal alloy.

18. The grain as claimed in claim 17, wherein said grain is made of titanium or titanium alloy.

19. An irregularly shaped grain as claimed in claim 17, wherein said multiple pores are filled with a decomposable material.

20. The grain as claimed in claim 19, wherein the decomposable material contains growth-stimulating substances.

21. The grain as claimed in claim 20, wherein said decomposable material includes a matrix of natural material.

22. The grain as claimed in claim 21, wherein said matrix of natural material includes a gel of at least one of collagen, fibrin, starch, hydroxylapatite or similar ceramics and hyaluronic acid.

23. An irregularly shaped grain as claimed in claim 17, wherein said grain has a coral structure.

24. The grain as claimed in claim 23, wherein said grain size is less than 10 mm.

25. An aggregate of grains consisting essentially of grains according to the grain of claim 17.

26. The aggregate as claimed in claim 25, wherein said aggregate of grains is configured for implant use.

27. An implant comprising a plurality of grains and a casing, said grains being made of a plastic or essentially non-elastic biocompatible material, wherein said grains include multiple pores that are continuous through the grain, and openings of said multiple pores and ducts or passages interconnecting at least a portion of said multiple pores have an average width of greater than about 10 μm, and wherein said grain is a metal or metal alloy.

28. The implant as claimed in claim 27, wherein the casing is a rigid cylindrical sleeve or a hollow fibre for producing a spinal implant.

29. The implant as claimed in claim 27, wherein said multiple pores of said grain are randomly distributed.

30. The implant as claimed in claim 27, wherein the multiple pores that are continuous are sized to allow the tissue to grow through said grain.

31. The implant as claimed in claim 27, wherein said grain is of a monolithic structure with said multiple pores extending into the surface of that monolithic structure.

* * * * *